United States Patent
Vincent et al.

(10) Patent No.: US 6,523,426 B1
(45) Date of Patent: Feb. 25, 2003

(54) WATER QUALITY MEASURING APPARATUS WITH A SENSING WAFER CLAMPED BETWEEN TWO O-RINGS

(75) Inventors: David Robert Vincent, Dorset (GB); John William Proctor, West Yorkshire (GB); Stuart Ward, Dorset (GB)

(73) Assignee: Siemens plc, Bracknell (GB)

( * ) Notice: Subject to any disclaimer, the term of this patent is extended or adjusted under 35 U.S.C. 154(b) by 0 days.

(21) Appl. No.: 09/646,004

(22) PCT Filed: Mar. 11, 1999

(86) PCT No.: PCT/EP99/01630

§ 371 (c)(1),
(2), (4) Date: Nov. 17, 2000

(87) PCT Pub. No.: WO99/46587

PCT Pub. Date: Sep. 16, 1999

(30) Foreign Application Priority Data

Mar. 11, 1998 (GB) .............................................. 9805014

(51) Int. Cl.[7] ........................ G01N 33/18; G01N 27/00; G01N 27/403
(52) U.S. Cl. ...................... 73/866.5; 73/866.1; 204/408
(58) Field of Search .............................. 73/866.5, 866.1, 73/53.01; 204/401, 406, 408

(56) References Cited

U.S. PATENT DOCUMENTS

| | | | | |
|---|---|---|---|---|
| 3,940,327 A | * | 2/1976 | Wagner et al. ............... 204/428 |
| 4,428,815 A | * | 1/1984 | Powell et al. ........... 204/297.03 |
| 4,689,122 A | * | 8/1987 | Polak et al. ............. 204/421 X |
| 4,912,600 A | | 3/1990 | Jaeger ........................ 361/385 |
| 5,111,699 A | * | 5/1992 | Walstra et al. ................. 73/754 |
| 5,120,421 A | * | 6/1992 | Gless et al. .................. 204/406 |
| 5,324,410 A | * | 6/1994 | Kummer et al. ........ 204/297.05 |
| 5,446,824 A | * | 8/1995 | Moslehi ....................... 392/416 |
| 5,763,787 A | * | 6/1998 | Gravel et al. .................. 73/756 |
| 5,827,985 A | * | 10/1998 | Grieger et al. ............. 73/866.5 |
| 6,030,709 A | * | 2/2000 | Jensen et al. ............. 73/706 X |
| 6,343,793 B1 | * | 2/2002 | Pitton et al. ................. 277/361 |

FOREIGN PATENT DOCUMENTS

| | | | | |
|---|---|---|---|---|
| DE | 3500088 | * | 7/1986 | .......... G01N/27/46 |
| EP | 644577 | * | 3/1995 | .......... H01L/21/00 |
| EP | 0801150 | | 2/2000 | ............. G01L/9/06 |
| GB | 2169412 | | 7/1986 | .......... G01N/27/56 |
| GB | 2283572 | * | 5/1995 | .......... G01N/33/18 |
| GB | 2290617 | * | 1/1996 | ......... G01N/27/403 |
| JP | 3-244550 | * | 11/1991 | .......... H01L/21/68 |
| WO | 89/05977 | * | 6/1989 | .......... G01N/33/53 |

\* cited by examiner

Primary Examiner—Thomas P. Noland
(74) Attorney, Agent, or Firm—Crowell & Moring LLP

(57) ABSTRACT

A device for water quality measurement apparatus includes a plurality of multi-element arrays formed on a substrate, which are immersed in a solution for detecting electroactive elements or compounds present in such a solution. A wafer is located between first and second 'O' rings, with the first 'O' ring being disposed on a first side of the wafer and the second 'O' ring being disposed on a second side of the wafer, opposite to the first side. The first and second 'O' rings are arranged such that the wafer is exposed to substantially equal pressure on both sides.

10 Claims, 4 Drawing Sheets

WATER QUALITY MEASURING APPARATUS WITH A SENSING WAFER CLAMPED BETWEEN TWO O-RINGS

BACKGROUND OF THE INVENTION

The present invention relates to water quality measurement apparatus. More specifically the present invention relates to an improved mechanical arrangement for water quality measurement apparatus.

The use of a plurality of electrochemical sensors deposited on a single wafer for the purpose of measuring multiple parameters of a liquid sample is well known. U.S. Pat No. 5,120,421 discloses an electrochemical sensor which comprises a plurality of multi-element arrays formed on a substrate, the sensor being immersed in a solution for detecting electroactive elements or compounds present in such a solution.

The main advantage of this type of sensor is that it is capable of measuring multiple parameters of a liquid sample. In addition, it is small, cheap to manufacture, and disposable. A primary use for such sensors is for on-line measurements to be made in a mains water pipe, thus eliminating the need to collect a sample and return to the laboratory for analysis, which is costly, time-consuming and often results in substantial errors in measurement accuracy.

To be able to conduct on-line, in-situ type measurements, the sensor must be exposed to the water in the pipe. This is achieved by a known technique in which a specially adapted mechanical device is fitted to the water pipe. This device allows for the sensor to be inserted into the pipe in such a way that the sensing area of the wafer is exposed to the water.

However, this known arrangement suffers from several disadvantages. Firstly the wafer is often inherently thin and may suffer damage or even rupture if exposed to different amounts of pressure. For example, if mains wafer pressure is present on one side of the wafer and atmospheric pressure present on the other side the difference between the two may cause the wafer to rupture. Secondly, any leakage of water from the sensor area to the electrical connectors can result in the sensor failing.

SUMMARY OF THE INVENTION

The present invention offers substantial improvements to the known methods in which wafer type sensors are held in place within the mechanical devices used with this type of water monitoring apparatus.

According to the present invention there is provided measuring apparatus including a wafer located between a first and a second 'O' ring, with said first 'O' ring being disposed on a first side of side of said wafer, and said second 'O' ring being disposed on a second side of said wafer, said second side being opposite to said first side, said first and said second 'O' rings being arranged such that in use a central portion of said first side of said wafer and a central portion of said second side of said wafer being of substantially the same diameter and opposite said central portion of said first side are exposed to substantially equal pressure and any remaining portions of said first and said second sides located outside said central portions are exposed to substantially equal pressure, said apparatus further including a mechanical device arranged to hold said wafer proximate a distal end thereof by means of said first 'O' ring and said second 'O' ring, said first and said second 'O' rings being removably attached to a first and a second 'O' ring holding means respectively, with said first 'O' ring holding means being substantially fixed to said distal end of said mechanical device, and said second 'O' ring holding means being substantially fixed to a detachable block means with said detachable block means being arranged to be held in place at said distal end of said mechanical device such that said wafer is held proximate said distal end of said mechanical device, characterised in that said first 'O' ring holding means further includes a plurality of pins disposed within a circular area defined by said first 'O' ring and which corresponds substantially with said central portion of said first side of said wafer, with said plurality of pins arranged to facilitate electrical contact between a plurality of electrical contact points disposed on said first side of said wafer and located within said central portion of said first side of said wafer and further electrical contacts disposed within said mechanical device.

In yet a further embodiment said first 'O' ring holding means includes a groove into which said first 'O' ring substantially fits.

In yet a fierier embodiment said second 'O' ring holding means includes a groove into which said second 'O' ring substantially fits.

Said plurality of pins may be spring loaded pins.

As will be appreciated by a person skilled in the art, said plurality of pins may be of a type other than spring loaded pin.

According to a further aspect of the present invention said wafer is substantially flat.

According to a further aspect of the present invention said wafer is substantially square.

According to yet a further aspect of the present invention said wafer includes a plurality of sensing devices disposed upon said first side of said wafer.

According to yet a further aspect of the present invention said plurality of sensors are disposed on both said first side and said second side of said wafer.

In yet a further aspect of the present invention said central portions of said wafer are exposed to equal amounts of atmospheric pressure and said remaining portions of said wafer are exposed to equal amounts of water pressure.

In yet a further aspect of the present invention said central portions of said wafer are prevented from being exposed to water.

By exposing each side of the wafer to substantially equal amounts of pressure, the wafer is less likely to rupture due to the effects of unequal amounts of pressure. For example, if the central portion of one side of the wafer was exposed to atmospheric pressure and the central portion of the opposite side was exposed to water pressure, the wafer is more likely to rupture due to the unequal pressure exerted on it then if both sides where exposed to equal amounts of either water or atmospheric pressure.

The apparatus according to the present invention advantageously allows for the wafer to be made thinner, while still being able to be used in applications which expose the wafer to higher pressures. Furthermore, the present invention advantageously allows for sensor devices to be disposed on both sides of said wafer.

While the principle application of the preferred embodiment of the present invention is as a water quality measurement apparatus, as will be appreciated by those skilled in the art, measurement of other types of anlaytes, such as solid, gases and liquids other than water, may be made without departing from the scope of the present invention.

While the principle advantages and features of the present invention have been described above, a greater understanding and appreciation of the invention may be obtained by referring to the following drawings and detailed description of a preferred embodiment, presented by way of example only.

DETAILED DESCRIPTION OF THE INVENTION

Figure 1:
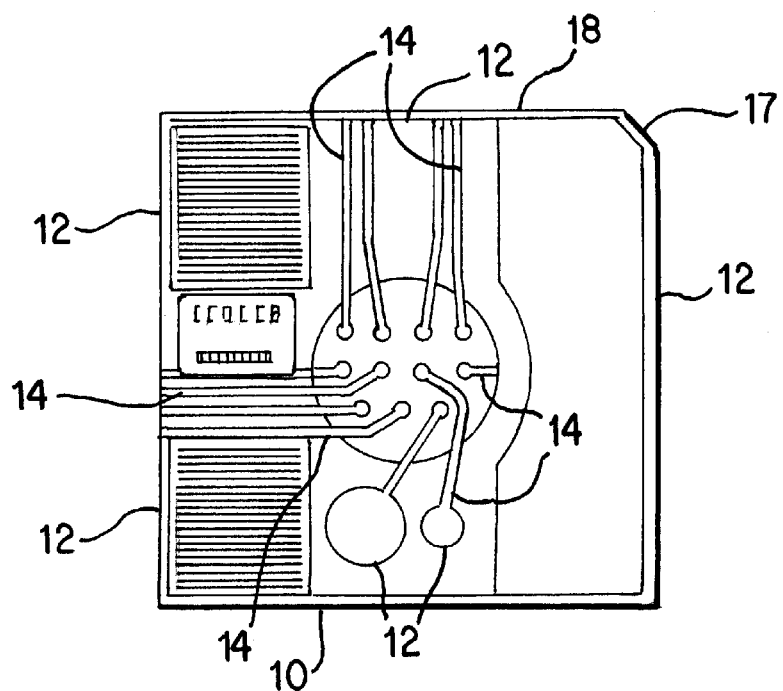
FIG. 1 is a diagram of a wafer type sensor according to one aspect of the present invention.

FIG. 1 shows a typical arrangement of a wafer according to a preferred embodiment of the present invention. In FIG. 1 a square wafer 10 is shown with a plurality of sensors 12 disposed on the surface. Each sensor 12 is connected by a lead 14 to a plurality of corresponding electrical contact points 16. As is well known in the art, the measurement of various electrochemical properties in a liquid sample can be achieved when a liquid sample comes into contact with the sensors 12. Known sensors are currently being used to measure various properties of a liquid sample such as dissolved oxygen, pH, temperature, and Chlorine and Ammonia levels. The operation of these types sensors is well known in the art, as disclosed in granted UK patents GB2283572 and GB2290617, which are hereby included as references.

The plurality of electrical contact point 16 are located within a central portion 18 of wafer 10. The plurality of sensor devices 12, leads 14 and electrical contact points 16 are deposited using techniques which are well known in the art such as thin and thick film deposition methods. The wafer 10 remains substantially flat despite the presence of sensors 12, leads 14 and contact points 16. The central portion 18 is the area of the wafer which is enclosed by a first 'O' ring when the wafer is held in place within the mechanical device.

In this preferred embodiment the wafer 10 is substantially square. A corner 17 of the wafer 10 is removed from the wafer. This allows for simplified alignment of the wafer within the mechanical device. As will be appreciated by those skilled in the art, the wafer 10 may be other shapes, such as circular or rectangular.

Figure 2:
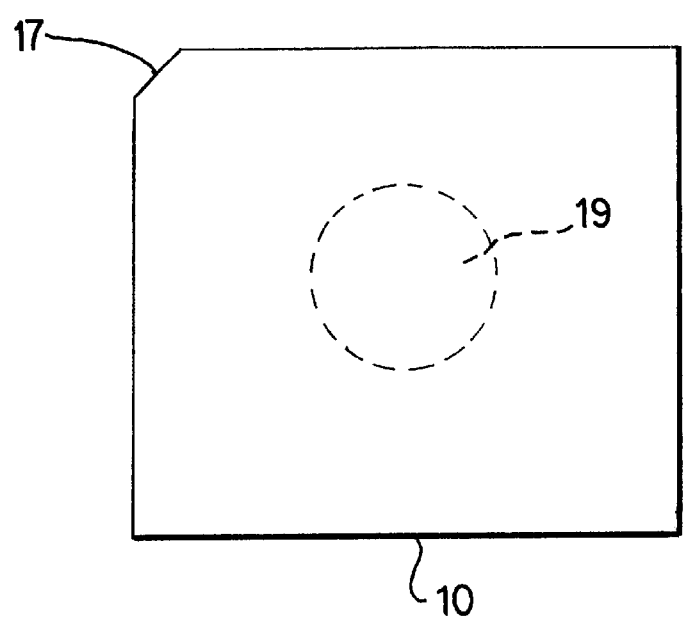
FIG. 2 is a diagram of the opposite side of the wafer shown in FIG. 1.

FIG. 2, where points also appearing in FIG. 1 bear identical numerical designation, shows the opposite side of the wafer 10 shown in FIG. 1. In FIG. 2 no sensors are disposed on this surface, however as would be appreciated by those skilled in the art, a plurality of sensors could be disposed on this surface. The central portion 19 of the wafer in FIG. 2 is substantially opposite to the central portion 18 of the wafer shown in FIG. 1. The central portion 19 is enclosed by a second 'O' ring when the wafer is held in place within the mechanical device. The effect of placing said first and second 'O' rings on opposite sides of the wafer is to expose the central portions 18 and 19 to equal amounts of pressure. Furthermore, the areas outside the central portion of the wafer are also exposed to equal amounts of pressure. The effect of equalising the pressure on either side of the wafer is to reduce the likelihood of the wafer rupturing during operation.

Figure 3:
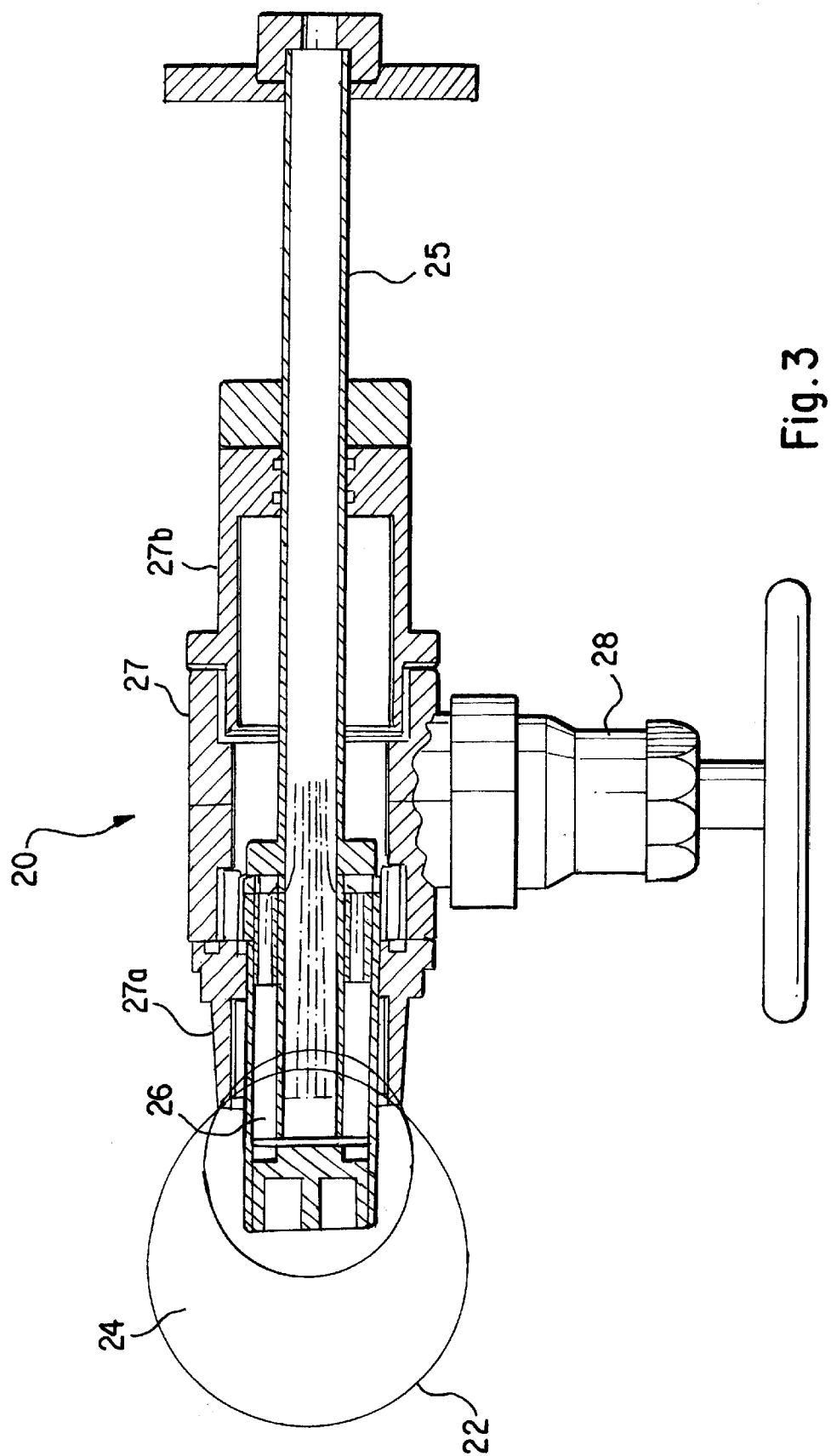
FIG. 3 is a diagram of the mechanical device used for inserting the wafer into water pipes.

FIG. 3, where parts also appearing in FIGS. 1 and 2 bear identical numerical designation, shows a mechanical device 20 attached to a pipe 22 for the purpose of allowing wafer 10 to be exposed to the water 24 flowing through pipe 22. The pipe may be a mains water pipe. The mechanical device 20 includes a probe head 26 and a centrally located hollow movable tube 25. The probe head 26 is disposed at the distal end of the hollow tube 25, which is inserted into a housing 27. The mechanical device 20 is attached to the pipe 22 at the probe head end and is held in place, for example, by a clamping or threading means (not shown), which are both well known in the art. The wafer 10 is attached to the probe head 26. The hollow tube allows for various electrical connections such as power to be made to the wafer.

The mechanical device 20 further comprises a valve means 28 which when in its closed position isolates the bottom end 27a from the top end 27b of the housing 27. The valve 28 can only be closed when the hollow tube 25 is withdrawn from the bottom end 27a of the housing 27. In operation, the hollow tube 25 may be withdrawn from the bottom end 27a of the housing 27 for maintenance purposes or to replace the wafer. When the valve 28 is in its open position the hollow tube 25 can be pushed into the pipe 22 where the wafer is exposed to water and measurements can be taken. FIG. 3 shows the mechanical device 20 in its measurement mode, with the probe head 26 and wafer 10 inserted into the bottom end 27a of the housing 27 and exposed to the water 24 located in the pipe 22.

Figure 4:
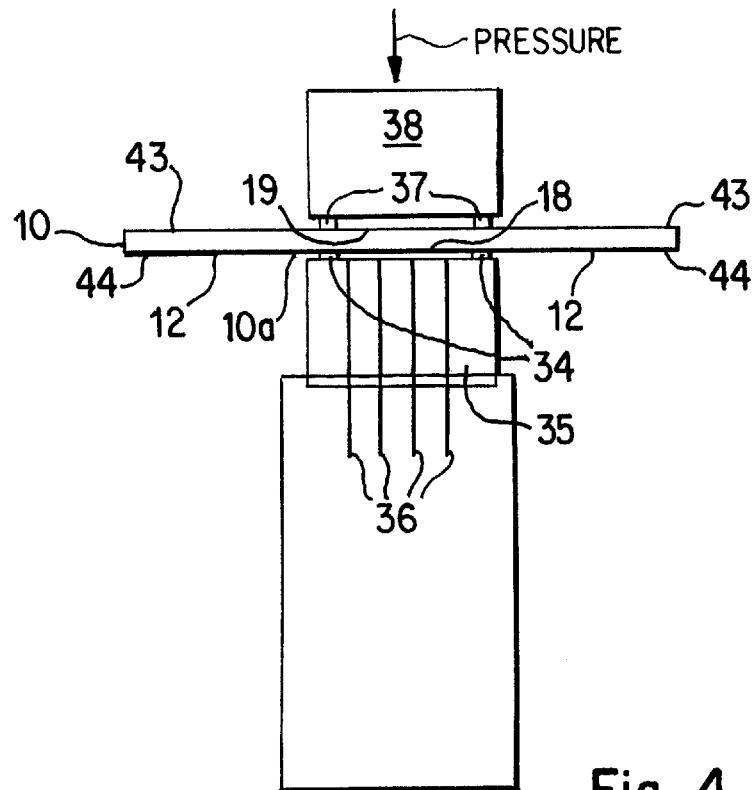
FIG. 4 shows a side view of the wafer held in place by the 'O' rings, according to a preferred embodiment of the present invention.

In FIG. 4, where parts also appearing in FIGS. 1, 2 and 3 bear identical numerical designation, a side view of wafer 10 is shown. A plurality of sensors 12 are disposed on the surface 10a of the wafer 10. The sensors are disposed outside the area defined by a centrally located first 'O' ring 34.

First 'O' ring 34 is removably attached to a first 'O' ring holding means 35. First 'O' ring holding means 35 may be made of metal or plastic or other suitable material. First 'O' ring holding means 35 may contain a groove (not shown) into which first 'O' ring 34 fits. A plurality of spring pins 36 are disposed on first 'O' ring holding means 35 and are located inside the diameter of first 'O' ring 34. The plurality of spring pins 36 are arranged to extend substantially perpendicular from first 'O' ring holding means 35 in a manner which facilitates electrical contact with the plurality of contact points 16 located on wafer 10.

A second 'O' ring 37 is removably attached to a second 'O' ring holding means 38 which may be made of metal or plastic or other suitable material. Second 'O' ring holding means 38 may contain a groove (not shown) into which second 'O' ring 37 fits.

Wafer 10 is held in place by the first and second 'O' rings 34 and 37 in a manner such that wafer areas 18 and 19 are exposed to substantially the same amount of pressure and wafer areas 43 and 44 are also exposed to substantially the same amount of pressure.

In this preferred embodiment, during operation, wafer areas 18 and 19 are exposed to atmospheric pressure and wafer areas 43 and 44 are exposed to water pressure. The water pressure will depend on the water pressure in the water pipe 24 to which mechanical device 20 is attached. The seal created by 'O' rings 34 and 37 with the wafer must be substantial enough to prevent leakage of water into wafer areas 18 and 19.

Figure 5:
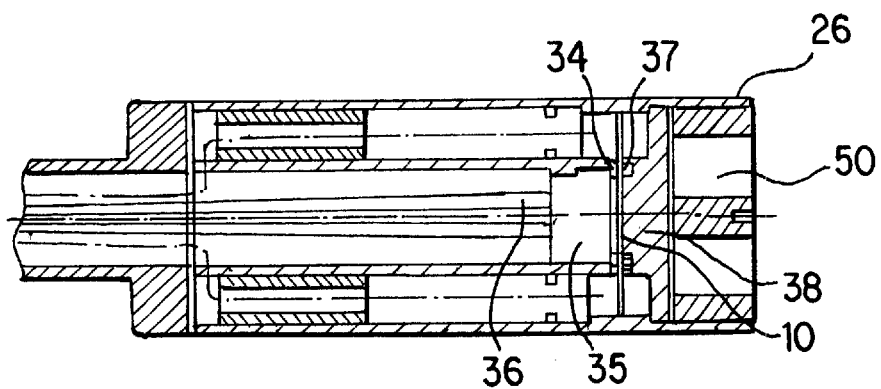
FIG. 5 shows a cross section of the probe head portion of the mechanical device shown in FIG. 3.
Figure 6C:
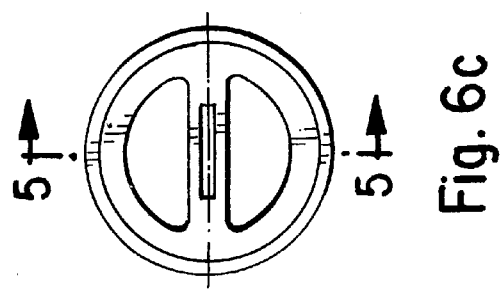
FIGS. 6a–c are respective end and side views of the probe head portion of FIG. 5.
Figure 6B:
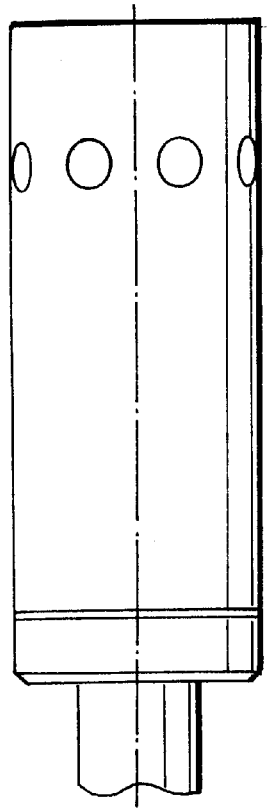
Figure 6A:
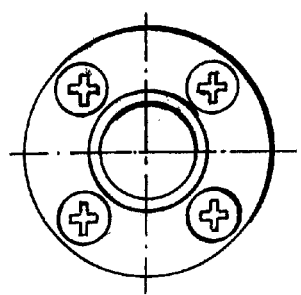

In FIG. 5, where points also appearing in FIGS. 1–4 bear identical numerical designation, a more detailed view of the probe head 26 is shown. The probe head 26 has an opening 50 at one end. Wafer 10 is inserted in the opening 50 such that the plurality of electrical contact points 16 make electrical contact with the plurality of spring pins 36. Second 'O' ring holding means 38 is then inserted into probe opening 50. The second 'O' ring holding means 38 is held in place in the probe head 26 via bayonet or thread means in a manner such that second 'O' ring 37 makes contact with the wafer. The second 'O' ring holding means 38 is designed such that water to be analysed can enter the probe head via openings 50 and make contact with the plurality of sensors 12 disposed on wafer 10. Spring pins 36 extend inside probe head 26 and make further electrical contact with various power and control electronics located outside the mechanical device.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Measuring apparatus comprising:
    a wafer located between first and second 'O' rings, said first 'O' ring being disposed on a first side of said wafer and said second 'O' ring being disposed on a second side of said wafer opposite to said first side, said first and said second 'O' rings being arranged such that in use a central portion of said first side of said wafer and a central portion of said second side of said wafer being of substantially the same diameter and opposite said central portion of said first side are exposed to substantially equal pressure and any remaining portions of said first and said second sides located outside said central portions are exposed to substantially equal pressure;
    a mechanical device arranged to hold said wafer proximate a distal end thereof by means of said first 'O' ring and said second 'O' ring, said first and said second 'O' rings being removably attached to a first and a second 'O' ring holding means respectively, with said first 'O' ring holding means being substantially fixed to said distal end of said mechanical device, and said second 'O' ring holding means being substantially fixed to a detachable block means which is arranged to be held in place at said distal end of said mechanical device, such that said wafer is held proximate said distal end of said mechanical device; wherein,
    said first 'O' ring holding means further includes a plurality of pins disposed within a circular area defined by said first 'O' ring and which corresponds substantially with said central portion of said first side of said wafer; and
    said plurality of pins are arranged to facilitate electrical contact between a plurality of electrical contact points disposed on said first side of said wafer and further electrical contacts disposed within said mechanical device.

2. Apparatus as claimed in claim 1, wherein said first 'O' ring holding means includes a groove into which said first 'O' ring substantially fits.

3. Apparatus as claimed in claim 1, wherein said second 'O' ring holding means includes a groove into which said second 'O' ring substantially fits.

4. Apparatus as claimed in claim 1, wherein said plurality of pins are spring loaded pins.

5. Apparatus as claimed in claim 1, wherein said wafer is substantially flat.

6. Apparatus as claimed in claim 1, wherein said wafer is substantially square.

7. Apparatus as claimed in claim 1, wherein said wafer includes a plurality of sensing devices disposed upon said first side of said wafer.

8. Apparatus as claimed in claim 7, wherein said plurality of sensors are disposed on both said first side and said second side of said wafer.

9. Apparatus as claimed in claim 1, wherein said central portions of said wafer are exposed to equal amounts of atmospheric pressure and said remaining portions of said wafer are exposed to equal amounts of water pressure.

10. Apparatus as claimed in claim 1, wherein said central portions of said wafer are prevented from being exposed to water.

* * * * *